United States Patent
Amelse

(10) Patent No.: US 10,266,462 B2
(45) Date of Patent: Apr. 23, 2019

(54) ENERGY EFFICIENT FRACTIONATION PROCESS FOR SEPARATING THE REACTOR EFFLUENT FROM TOL/A9+ TRANSALKYLATION PROCESSES

(71) Applicant: BP Corporation North America Inc., Houston, TX (US)

(72) Inventor: Jeffrey Amelse, Batavia, IL (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 15/118,572

(22) PCT Filed: Feb. 4, 2015

(86) PCT No.: PCT/US2015/014465
§ 371 (c)(1),
(2) Date: Aug. 12, 2016

(87) PCT Pub. No.: WO2015/123065
PCT Pub. Date: Aug. 20, 2015

(65) Prior Publication Data
US 2017/0050901 A1 Feb. 23, 2017

Related U.S. Application Data

(60) Provisional application No. 61/939,314, filed on Feb. 13, 2014.

(51) Int. Cl.
*C07C 7/04* (2006.01)
*C07C 6/12* (2006.01)
(Continued)

(52) U.S. Cl.
CPC ............... *C07C 7/04* (2013.01); *B01D 3/143* (2013.01); *B01D 9/0059* (2013.01); *B01D 15/10* (2013.01);
(Continued)

(58) Field of Classification Search
None
See application file for complete search history.

(56) References Cited

U.S. PATENT DOCUMENTS 3,584,068 A 6/1971 Jackson et al.
3,927,135 A * 12/1975 Suggitt .................. C07C 15/02
208/62
(Continued)

FOREIGN PATENT DOCUMENTS

| | | |
|---|---|---|
| CN | 101198573 | 6/2008 |
| CN | 103664489 | 3/2014 |
| RU | 2167139 | 6/1999 |

OTHER PUBLICATIONS

Anton Kiss et al.—Intensified process for aromatics separation powered by kaibel and diving-wall colums.
(Continued)

*Primary Examiner* — Tam M Nguyen
(74) *Attorney, Agent, or Firm* — Robert N. Carpenter

(57) ABSTRACT

Processes and apparatus are disclosed for the energy efficient separation of the effluent from a TOL/A9+ transalkylation reactor. The apparatus includes a reboiled prefractionation column and a sidedraw tower that produces: 1) an overhead stream including unreacted toluene, 2) a stream including unreacted C9+ aromatics, a portion of which stream may be recycled to the reactor; and 3) a sidedraw stream including C8 aromatics that may be directed to a crystallization or selective adsorption paraxylene separation unit for recovery o a paraxylene product.

7 Claims, 2 Drawing Sheets

(51) Int. Cl.
    *B01D 3/14*     (2006.01)
    *B01D 9/00*     (2006.01)
    *B01D 15/10*    (2006.01)
(52) U.S. Cl.
    CPC ...... *C07C 6/126* (2013.01); *B01D 2009/0086* (2013.01); *Y02P 20/57* (2015.11)

(56) References Cited

U.S. PATENT DOCUMENTS

| | | | | |
|---|---|---|---|---|
| 4,246,073 | A * | 1/1981 | Umeda | B01D 3/146 |
| | | | | 203/25 |
| 4,419,188 | A * | 12/1983 | McCall | B01D 3/007 |
| | | | | 203/24 |
| 4,594,145 | A * | 6/1986 | Roarty | C10G 59/06 |
| | | | | 208/133 |
| 4,744,869 | A * | 5/1988 | Saito | B01D 3/143 |
| | | | | 203/82 |
| 5,953,936 | A * | 9/1999 | Agrawal | B01D 3/146 |
| | | | | 62/630 |
| 6,250,106 | B1 | 6/2001 | Agrawal | |
| 6,417,420 | B1 * | 7/2002 | Stewart | B01D 3/141 |
| | | | | 585/323 |
| 6,479,720 | B1 | 11/2002 | O'Brien et al. | |
| 7,169,368 | B1 | 1/2007 | Sullivan et al. | |
| 7,179,434 | B1 | 2/2007 | Maher et al. | |
| 7,267,746 | B1 | 9/2007 | Harris et al. | |
| 9,708,233 | B2 * | 7/2017 | Molinier | C07C 5/2732 |
| 2005/0228206 | A1 * | 10/2005 | Amelse | B01D 9/0013 |
| | | | | 585/812 |
| 2006/0287563 | A1 | 12/2006 | Schultz et al. | |
| 2008/0262280 | A1 | 10/2008 | Casey et al. | |
| 2009/0036724 | A1 | 2/2009 | Negiz et al. | |
| 2011/0172458 | A1 | 7/2011 | Merenov et al. | |
| 2011/0303526 | A1 | 12/2011 | Lee et al. | |
| 2012/0006673 | A1 * | 1/2012 | Lee | B01D 3/14 |
| | | | | 203/87 |
| 2012/0271084 | A1 | 10/2012 | Haizmann et al. | |
| 2013/0261365 | A1 | 10/2013 | Wang et al. | |
| 2015/0299075 | A1 * | 10/2015 | Lee | C07C 29/80 |
| | | | | 203/22 |
| 2016/0200650 | A1 * | 7/2016 | Park | B01D 61/362 |
| | | | | 568/913 |
| 2016/0207858 | A1 * | 7/2016 | Park | C07C 29/76 |
| 2018/0178141 | A1 * | 6/2018 | Lee | B01D 3/32 |

OTHER PUBLICATIONS

Nickos P. Doukas et al.—Control fo Energy-Conserving Prefractionator/Sidestream Column Distillation System, (1980), pp. 147-153.
Anton Kiss et al.—Energy efficient control of BTX dividing-wall column, vol. 35.
M. Shamsuzzoha et al.—Design and Analysis of Divided Wall Column pp. 397-402.
Salvador Hernadez et al.—Thermodynamically equipment distillation schemes to the petlyuk column for ternary mixtures, pp. 2176-2183, Energy 31.
Ning Wu, et al.—Operation of Dividing-Wall Distillation Columns. 2. A Double Temperature Difference Control Scheme pp. 5365-5383.
Yufeng Wang, et al.—Circumventing the Black-Hole Problem in Design and Control of Dividing-Wall Distillation Colums, pp. 14771-14792.
C.S. Bildea et al. Interaction between design and control of a heat-integrated distillation system with prefractionator, pp. 597-608. vol. 77, Part A. vol. 77, Issue 7.
Uwitonze Hosanna et al.—Fully thermally coupled distillation column design using Kremser approximate group methods, pp. 968-974.
I. Dejanovic et al.—An effective method for establishing the stage and reflux requirment of three-product dividing wall colums, pp. 147-157.
Michael A. Schultz et al.—Reduce Costs with dividing-wall columns, pp. 64-71, Reactions and Separations.
Beatriz Brignole et al.—Dynamics and cotrol of a distillation train without recycle streams, pp. 1875-1889.
Cheng et al.—Heat-integrated distillation columns for ternary separations, pp. 707-713.
Elaine Chang et al.—Xylene Separation, SRI Consulting, Mar. 1998.
Robert A. Meyers—Handbook of Petroleum Refining Processes, Thrid Edition, The McGraw-Hill Companies (Chapter 2.1, Aromatics Complexes), pp. 2.3-2.11.
Robert A. Meyers—Handbook of Petroleum Refining Processes, Thrid Edition, The McGraw-Hill Companies (Chapter 2.5, UOP Isomar Process), pp. 2.39-2.46.
Robert A. Meyers—Handbook of Petroleum Refining Processes, Thrid Edition, The McGraw-Hill Companies (Chapter 2.6, UOP Parex Process), pp. 2.47-2.54.
Robert A. Meyers—Handbook of Petroleum Refining Processes, Thrid Edition, The McGraw-Hill Companies (Chapter 2.7, UOP Tatoray Process), pp. 2.55-2.63.
Robert A. Meyers—Handbook of Petroleum Refining Processes, Thrid Edition, The McGraw-Hill Companies (Chapter 2.2, UOP Sulfolane Process), pp. 2.13-2.23.
I. Dejanovic et al.—Dividing wall—a breakthrough toward sustainable distilling, pp. 560-580.
Nick Austin et al.—Computer-aided molecular design: An introduction and review of tools, applications, and solution techniques, pp. 2-26, 116.
Erik A. Wolff, et al.—Operation of Integrate Three-Product (Petlyuk) Distillation Colums, pp. 2094-2103.

* cited by examiner

ENERGY EFFICIENT FRACTIONATION PROCESS FOR SEPARATING THE REACTOR EFFLUENT FROM TOL/A9+ TRANSALKYLATION PROCESSES

CROSS-REFERENCE TO RELATED APPLICATION

This application claims priority to U.S. Provisional Application No. 61/939,314, filed Feb. 13, 2014, which is hereby incorporated by reference in its entirety.

BACKGROUND

Aromatics complexes generally derive their feed from a catalytic reformer, although other sources of mixed xylenes feeds are possible, such as those derived from pyrolysis gasoline from olefin crackers. The reformate product from the reformer contains benzene (Bz), toluene (TOL), C8 aromatics (ethylbenzene (EB), and the three xylene isomers of paraxylene (pX), metaxylene (mX), and orthoxylene (oX)), and C9+ aromatics that are primarily C9 and to a lesser extent C10+ aromatics. Most aromatics complexes focus on the production of paraxylene and benzene, and occasionally orthoxylene and metaxylene, although the markets for orthoxylene and metaxylene are not as large as for paraxylene. Paraxylene is oxidized to terephthalic acid which is purified and polymerized with ethylene glycol to make polyester. Polyester is used in making clothing, film and bottles. Benzene is used in making many useful derivatives with end products such as polystyrene, nylon, polycarbonate, and phenolic resins.

To make the most amount of paraxylene and benzene from a given amount of reformate, aromatics complexes may comprise units that will convert the toluene and/or C9+ aromatics in the reformate to xylenes and benzene, including TOL/A9+ transalkylation (TOL/A9+ TA) units.

TOL/A9+ transalkylation usually takes place in the presence of hydrogen. Processing C9+ aromatics is complex, because there are a number of A9 and A10 isomers that can undergo a number of different reactions depending on the choice of catalyst. Reactions occurring in a TOL/A9+ transalkylation (TA) reactor include but are not limited to:

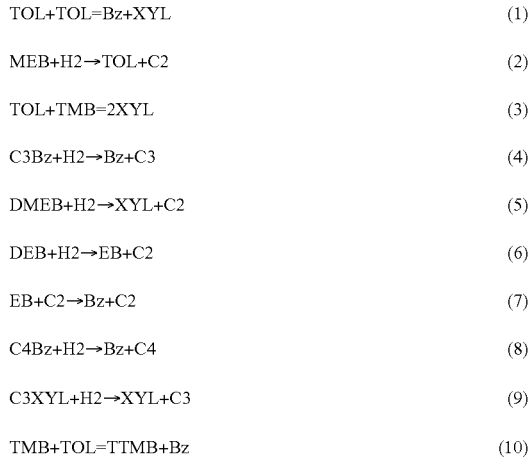

Where:
XYL=xylene isomers
MEB=methylethylbenzenes (3 isomers)
TMB=trimethylbenzenes (three isomers)
C3Bz=propylbenzenes (iso-propylbenzene=cumene and n-propylbenzene)
H2=hydrogen
C2=ethane
C3=propane
DMEB=dimethylethylbenzenes (6 isomers)
DEB=diethylbenzenes (3 isomers)
C4Bz=butylbenzenes (4 isomers)
C3XYL=propylxylenes (includes n-proylxylenes and iso-propylxylenes known as cymenes)
TTMB=tetramethylbenzenes (3 isomers)

Note that MEB hydrocracking (Reaction 2) produces TOL, which can react with TMB to form xylenes (Reaction 3) or disproportionate to form xylenes and benzene (Reaction 1). Thus, A9+ can be a feed to a TOL/A9+ reactor alone, i.e., TOL in the feed can be zero.

MEB and propylbenzene hydrocracking (Reactions 2 and 4) can be driven to very high conversion. However, transalkylation reactions that produce xylene isomers (such as Reactions 1 and 3) are equilibrium limited. Thus, the reactor effluent from TOL/A9+ TA will contain light ends, including C2 and C3, Bz, XYL, and unreacted TOL and A9+. The reactor effluent is separated into streams rich in light ends, Bz, XYL, and unreacted TOL and A9+. The TOL and components of the A9+ are recycled to the reactor. Separation of the reactor effluent into these streams is energy intensive and represents a substantial portion of the variable cost for these processes.

Accordingly, there remains the need for other energy and capital efficient schemes for separating the reactor effluent from TOL/A9+ transalkylation reactors.

SUMMARY

The present disclosure addresses the energy efficient separation of the effluent from a TOL/A9+ TA reactor into streams concentrated in light ends, benzene, TOL, A8, and A9+. In one aspect, the disclosure is directed to a process that includes (a) providing a prefractionation column feed stream including toluene, C8 aromatics, and C9+ aromatics to a reboiled prefractionation column to produce a prefractionation column top stream and a prefractionation column bottom stream; and (b) providing the prefractionation column top stream and the prefractionation column bottom stream to a sidedraw column to produce a sidedraw column top stream including toluene, and a sidedraw column first side stream including C8 aromatics. The process may also include producing a sidedraw column bottoms stream including C9+ aromatics. Alternatively, the process many include producing a sidedraw column second side stream including A9 for recycle to a TOL/A9+ transalkylation reactor without further fractionation, and a C10+ sidedraw column bottoms stream that is substantially free of A9.

In various aspects of the disclosure, the process includes recovering paraxylene from the sidedraw column first side stream including C8 aromatics to produce a paraxylene product stream and a paraxylene lean stream.

In one particular aspect of the disclosure a benzene column feed stream including benzene, toluene, C8 aromatics, and C9+ aromatics is provided to a benzene column to produce a benzene column top stream including benzene and a benzene column bottom stream including toluene, C8 aromatics, and C9+ aromatics, wherein the benzene column bottom stream is the prefractionation column feed stream.

In another aspect, the benzene column feed stream is obtained by the process including providing a stabilizer column feed stream including light ends, benzene, toluene, C8 aromatics, and C9+ aromatics to a stabilizer column to produce a stabilizer column top stream or streams including light ends and a stabilizer column bottom stream including benzene, toluene, C8 aromatics, and C9+ aromatics, wherein the stabilizer column bottom stream is the benzene column feed stream.

In these and other aspects of the disclosure, the process may include mixing a transalkylation reactor effluent stream including light ends, benzene, toluene, C8 aromatics, and C9+ aromatics with a paraxylene unit stream including benzene and toluene to produce the stabilizer column feed stream.

In one aspect, the process includes operating the sidedraw column at a pressure above atmospheric pressure and using the condensing vapors in the sidedraw column top stream to generate steam, to reboil the benzene column, and/or reboil the stabilizer column.

Another embodiment of the disclosure is directed to an apparatus that includes a reboiled prefractionation column for receiving a prefractionation feed stream including toluene, C8 aromatics, and C9+ aromatics and producing a prefractionation column top stream and a prefractionation column bottom stream; and a sidedraw column for receiving the prefractionation column top stream and the prefractionation column bottom stream and producing a sidedraw column top stream including toluene, and a sidedraw column first side stream including C8 aromatics. In various aspects of this embodiment, the sidedraw column further produces a sidedraw column bottoms stream including C9+ aromatics. Alternatively, the sidedraw column further produces a sidedraw column second sidedraw stream including A9 for recycle to a TOL/A9+ transalkylation reactor without further fractionation, and a C10+ sidedraw column bottoms stream that is substantially free of A9.

In another aspect, the apparatus includes a benzene column for receiving a benzene column feed stream including benzene, toluene, C8 aromatics, and C9+ aromatics, and separating the benzene column feed stream into a benzene column top stream including benzene and a benzene column bottom stream including toluene, C8 aromatics, and C9+ aromatics, wherein the benzene column bottom stream is the prefractionation column feed stream.

The apparatus may also include a stabilizer column for receiving a stabilizer column feed stream including light ends, benzene, toluene. C8 aromatics, and C9+ aromatics, and producing a stabilizer column top stream including light ends and a stabilizer column bottom stream including benzene, toluene, C8 aromatics, and C9+ aromatics; wherein the stabilizer column bottom stream is the benzene column feed stream.

The apparatus may also include a mixer for mixing a transalkylation reactor effluent stream including light ends, benzene, toluene, C8 aromatics, and C9+ aromatics with a paraxylene unit stream including benzene and toluene to produce the stabilizer column feed stream.

In yet another embodiment, the disclosure is directed to a process including the steps of: reacting in a transalkylation reactor a reactor feed stream including toluene and, optionally, C9+ aromatics to produce a transalkylation reactor effluent stream including light ends, benzene, toluene, C8 aromatics, and C9+ aromatics; optionally mixing the transalkylation reactor effluent stream with a paraxylene unit stream including benzene and toluene to produce a stabilizer column feed stream including light ends, benzene, toluene, C8 aromatics, and C9+ aromatics; separating the stabilizer column feed stream in a stabilizer column to produce a stabilizer column top stream including light ends and a stabilizer column bottom stream including benzene, toluene, C8 aromatics, and C9+ aromatics; separating the stabilizer column bottom stream in a benzene column to produce a benzene column top stream including benzene and a benzene column bottom stream including toluene, C8 aromatics, and C9+ aromatics; providing the benzene column bottom stream to a reboiled prefractionation column to produce a prefractionation column top stream and a prefractionation column bottom stream; providing the prefractionation column top stream and the prefractionation column bottom stream to a sidedraw column to produce a sidedraw column top stream including toluene, and a sidedraw column first side stream including C8 aromatics; recovering paraxylene from the sidedraw column side stream including C8 aromatics; and recovering benzene from the benzene column top stream, wherein at least a portion the sidedraw column top stream containing toluene and a sidedraw column stream containing C9+ aromatics is recycled to the transalkylation reactor.

Figure 1:
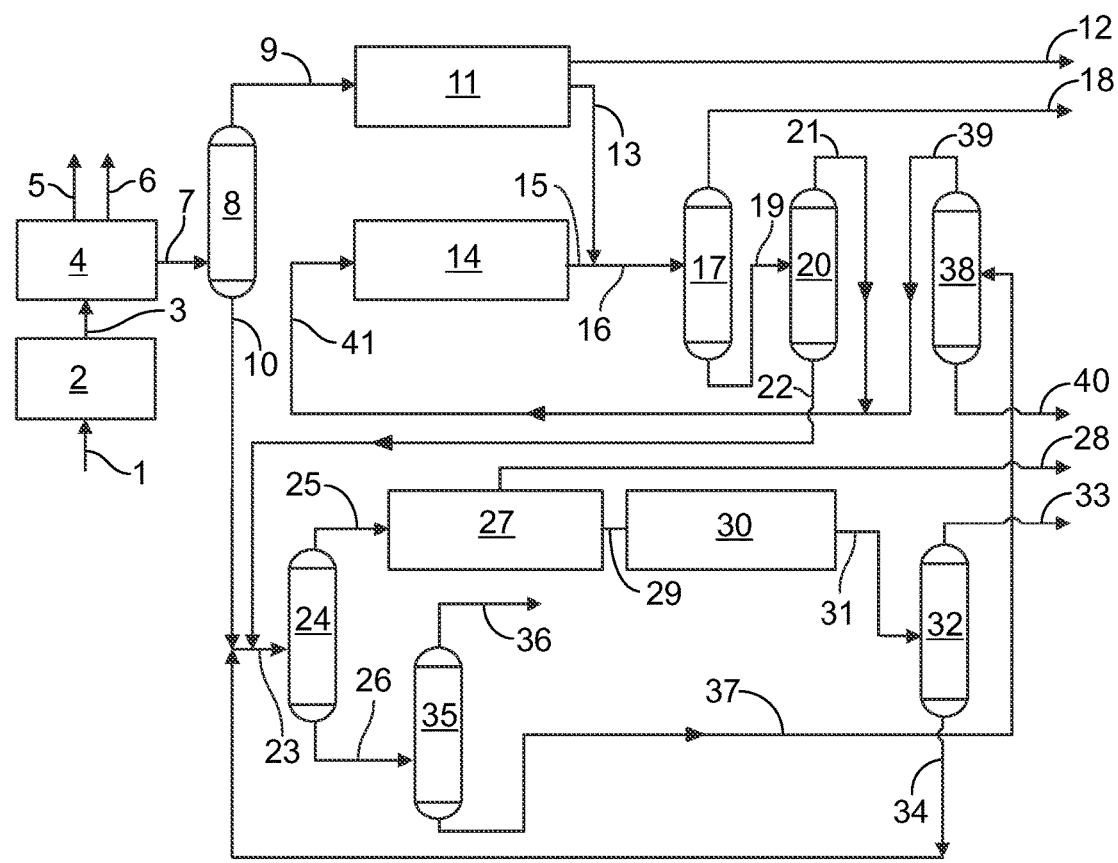
FIG. 1 shows an integrated aromatics complex for paraxylene recovery by a PAREX™ selective adsorption process. The effluent from the TOL/A9+ transalkylation reactor is separated into streams concentrated in benzene, TOL, C8A, and C9A+ by separate sequential Bz, TOL, Xylene Splitter and A9 columns.

Skilled artisans will appreciate that elements in the figures are illustrated for simplicity and clarity and have not necessarily been drawn to scale. For example, the dimensions of some of the elements in the figures can be exaggerated relative to other elements to help improve understanding of the embodiment(s) of the present invention. Skilled artisans will also understand that certain elements within these figures may represent sections of an aromatics complex that comprise many unit operations and equipment, such as reactors, pumps, distillation columns, pumps, compressors, heat exchangers, and separation equipment such as filters, centrifuges, selective adsorption chambers, and the like.

DESCRIPTION

The disclosure relates to an energy efficient fractionation process for separating a TOL/A9+ transalkylation (TA) reactor effluent into streams concentrated in light ends, benzene, a stream concentrated in TOL that can be recycled to the reactor, a stream concentrated in C8 aromatics (A8 or C8A) that can be sent directly to a crystallization or selective adsorption paraxylene recovery unit without the need for additional fractionation, and an A9+ stream that can be optionally further fractionated to recover C9 aromatics (A9 or C9A) and C10 aromatics (A10 or C10A) for recycle to the TOL/A9+ TA reactor.

The methods and apparatuses disclosed herein provide certain advantages and advancements over the prior art. As one example, light ends and benzene are separated in a stabilizer column and a benzene column respectively. Then benzene column bottoms including TOL, A8, and A9+(TOL/A8/A9+) are separated into separate streams rich in those components using an apparatus including a reboiled prefractionation column and a sidedraw column that produces: 1) an overhead stream concentrated in TOL; 2) a stream concentrated in A9+, which streams may be recycled to the reactor; and 3) a sidedraw stream concentrated in A8 and substantially free of benzene, TOL, and A9+ that can be directed to a crystallization or selective adsorption pX separation unit for recovery of pX product. The pressure of the reboiled prefractionation column and the sidedraw column may be increased such that the condensing overhead vapors of the sidedraw column may be used to reboil the stabilizer and/or benzene column and optionally may be used to generate stream. The overhead vapor of the prefractionation column may be fed to the sidedraw column without condensation, thus eliminating the need for a condenser, reflux drum, and associated equipment. An additional sidedraw may be taken from the sidedraw column concentrated in A9 and optionally A10 that may be recycled to the reactor. In this case, the sidedraw column bottoms includes C10+ hydrocarbons that may be used for fuel, or other uses. This avoids the need for a separate A9 column and saves additional energy.

Those skilled in the art will appreciate that the designator "CX" refers to a compound including X carbon atoms, "CX+" refers to a compound including X or greater carbon atoms, and "CX−" refers to a compound including X or fewer carbon atoms. The term "AX" is used to designate a stream including aromatics having X carbon atoms. For example, A9+ may be used to designate a stream including aromatics having nine or more carbon atoms. "CX aromatics" or "CXA" refers to a mixture of aromatic and nonaromatic compounds having X atoms. Accordingly, for example, "C8 aromatics" or "C8A" means designates a stream of aromatic and non-aromatic compounds having 8 carbon atoms. Similarly, "C8+" may contain some A8+ and non-aromatics with more 8 or more carbon atoms.

Mixed xylenes is a term used for a stream including not only the xylene isomers, but also ethylbenzene (EB), which has the same molecular formula as the xylene isomers ($C_8H_{10}$), but which is a structural isomer that has one ethyl group attached to a benzene, instead of two methyl groups in the case of the xylene isomers. There are three isomers of xylenes: orthoxylene (oX), metaxylene (mX), and paraxylene (pX). Collectively, the xylene isomers and EB are called C8 Aromatics or C8A. The boiling points of the C8A are very close, and thus, it is not practical or economic to separate pX from mixed xylenes by distillation. Thus, pX is separated from C8A by processes such as crystallization or pX selective adsorption.

As used herein, the phrase "substantially free of" generally refers to less than about 2 wt % of a component, more particularly less than about 1.5 wt % of the component, for example less than about 1.0 wt % of the component if the pX separation unit is a crystallization unit. In one embodiment, if the pX separation unit is a pX selective adsorption unit, substantially free of A9+ means less than about 500 ppmw, about 400 ppmw, about 300 ppmw, about 200 ppmw, or 100 about ppmw of A9+ or as otherwise required for the feed stream to the pX separation unit.

As used herein, the phrase "a stream concentrated in an aromatic component (or components)" refers to a stream including those components and substantially free of other aromatic components. For example, a stream concentrated in benzene means a stream including mainly benzene and substantially free of TOL, A8, and A9+. A stream concentrated in C8A+ means a stream including mainly C8A and C9A+ but substantially free of benzene and TOL.

An aromatics complex including a scheme for separating the reactor effluent from a TOL/A9+ TA unit is illustrated in FIG. 1. This aromatics complex includes several process units including a naphtha hydrotreater (NHT); a reformer, such as a UOP CCR PLATFORMING™ unit; an extraction unit, such as a UOP SULFOLANE™ Extraction unit; a TOL/A9+ TA unit, such as a UOP TATORAY™ unit; a paraxylene unit that further includes a xylene isomerization unit, such as a UOP ISOMAR™ unit for isomerizing xylene isomers and converting ethylbenzene (EB); a pX selective adsorption unit, such as a UOP PAREX™ unit; and distillation columns for separating the reactor effluent from the TOL/A9+ TA unit and the xylene isomerization unit into streams rich in benzene, TOL, C8A, and C9A+. A further description of various aspects this aromatics complex and the units that comprise it can be found in R. A. Meyers, editor, Handbook of Petroleum Refining Processes, $3^{rd}$ Edition, Mc-Graw-Hill (2004), which is incorporate herein in its entirety.

In FIG. 1, a naphtha stream (Stream 1) that includes C6-C10 paraffins and naphthenes is fed to a naphtha hydrotreater (NHT) unit 2. The NHT unit 2 includes a reactor that reacts sulfur and nitrogen containing compounds with hydrogen (stream not shown) and typically removes the sulfur and nitrogen compounds as light gaseous products such as hydrogen sulfide and ammonia (also not shown). The hydrotreated naphtha steam (Stream 3) is sent to a reformer 4. The reformer unit 4 includes a reactor that cyclizes straight chain and branched paraffins to form naphthenes and dehydrogenates the naphthenes to form aromatic compounds. The reformer generates a stream rich in hydrogen 5 and light ends 6, and a stream including C5+ hydrocarbons (Stream 7) that is rich in aromatics including benzene, toluene, C8 aromatics, and C9+ aromatics. The Stream 7 is fed to a reformate splitter column 8. The reformate splitter column 8 generates an overhead stream (Stream 9) rich in C7-hydrocarbons that includes benzene and toluene, and a bottom stream including C8+ aromatics (Stream 10). Stream 9 is fed to an extraction unit 11 that separates a raffinate stream (Stream 12) including mainly C5-C7 non-aromatics that is lean in aromatics and extract stream (Stream 13) that is rich in benzene and toluene and is substantially free of non-aromatics. Stream 13 is combined with the liquid effluent from a TOL/A9+ transalkylation (TA) unit 14. The TOL/A9+ TA unit 14 includes a reactor that converts at least a portion of the TOL and A9+ to products including benzene and xylene isomers via reactions including Reactions 1-10 (above). The TOL/A9+ unit 14 consumes hydrogen from a hydrogen rich feed stream (not shown), and generates light ends (not shown). The light ends may be removed by a stabilizer (not shown), which may be part of the TOL/A9+ unit.

The stabilized reactor effluent from the TOL/A9+ TA unit 14 (Stream 15) includes benzene, unreacted TOL, C8A, and unreacted C9A+. Stream 15 is combined with the stream from the extraction unit 11 (Stream 13) to produce Stream 16. The benzene, TOL, C8A, and C9A+ in combined Stream 16 are separated in sequential benzene, toluene, xylene splitter, and A9 distillation columns 17, 20, 24, and 38. FIG. 1 shows optional co-production of an orthoxylene product as the overhead of oX column 35.

Stream 16 is directed to a benzene column 17, which produces an overhead stream including benzene (Benzene Product Stream 18) and is substantially free of other aromatics, and bottoms stream (Stream 19) including C7+ aromatics. Stream 19 is directed to a TOL column 20, which produces an overhead stream (Stream 21) including TOL and substantially free of other aromatics that is directed to the TOL/A9+ TA unit 14, and bottoms stream (Stream 22) including C8+ aromatics.

Stream 22 is mixed with a deheptanizer column 32 bottoms stream (Stream 34) and the reformate splitter 8 bottoms stream (Stream 10) to form a feed stream (Stream 23) directed to xylene splitter column 24. The column 24 produces an overhead stream including C8A and some TOL (Stream 25) and substantially free of other aromatics and a bottoms stream (Stream 26) including C9A+, and in this case including a substantial fraction of the oX in combined xylene splitter column feed stream (Stream 23). Orthoxylene is produced as an overhead product of column 35. Co-production of oX within an aromatics complex is optional. The bottoms of column 35 comprising A9+ is directed to A9 column 38 which produces an overhead stream 39 comprising A9 and typically some A10 that is recycled to the TOL/A9+ TA unit. The bottoms of column 38 comprising C10+ is taken as a product for use as fuel, for example, or for other uses.

In one embodiment of the scheme shown in FIG. 1, the condensing vapors of the xylene splitter (XS) in an aromatics complex including a PAREX™ pX selective adsorption unit can be used to reboil the extract and raffinate columns within the PAREX™ section (which are not shown). Thus, there may not be enough additional heat available in the condensing XS overhead vapors to reboil the TOL/A9+ transalkylation unit benzene column or toluene column.

Stream 25 is directed to a pX recovery unit 27 such as a UOP PAREX™ unit, which produces a high purity pX product (Stream 28), and a raffinate stream (Stream 29) that is lean in pX. When the pX recovery unit is a UOP PAREX™ unit, it may also produce a stream rich in TOL (not shown) from co-adsorbed TOL that can be directed to the TOL/A9+TA unit 14, pX lean raffinate stream (Stream 29) is directed to a xylene isomerization unit 30 that includes a reactor that isomerizes the xylenes in the pX lean raffinate to a near equilibrium distribution, and converts at least a portion of the EB to xylene isomers, or benzene and ethane. Xylene isomerization catalysts that convert EB primarily to xylene isomers or to benzene and ethane are well known to those skilled in the art. Xylene isomerization and EB conversion reactions usually take place in the vapor phase, consume hydrogen from a hydrogen rich feed stream (not shown) and may generate a hydrogen rich vent stream (not shown). However, xylene isomerization and EB conversion processes are known that are conducted in the liquid or supercritical phases without the addition of hydrogen.

The reactor effluent (Stream 31) from the xylene isomerization unit 30 may be directed to the deheptanizer column 32 that produces a C7− stream (Stream 33). Stream 33 may be a vapor stream, a liquid stream, or both. Stream(s) 33 may comprise benzene and TOL, and may be further stabilized to remove light ends before directing to the benzene column 17 or the extraction unit 11 to recover benzene as product and TOL for recycle to the TOL/A9+ TA unit 14. This stabilizer is not shown in FIG. 1.

A deheptanizer bottoms stream (Stream 34) includes C8A+. This stream is combined with reformate splitter bottoms stream (Stream 10), and TOL column 20 bottoms stream (Stream 22), which are also comprise C8A+, and directed to the xylene splitter column 24.

A xylene splitter bottoms stream (Stream 26) may be directed to an oX column 35 that produces an oX product overhead stream (Stream 36) and a bottoms stream (Stream 37) including A9+. Stream 37 is directed to an A9 column 38 which produces a bottoms stream (Stream 40) including C10+ that may be taken as a product for use as, for example, a fuel, and an overhead stream (Stream 39) including A9+ that can be directed to the TOL/A9+ TA unit.

Figure 2:
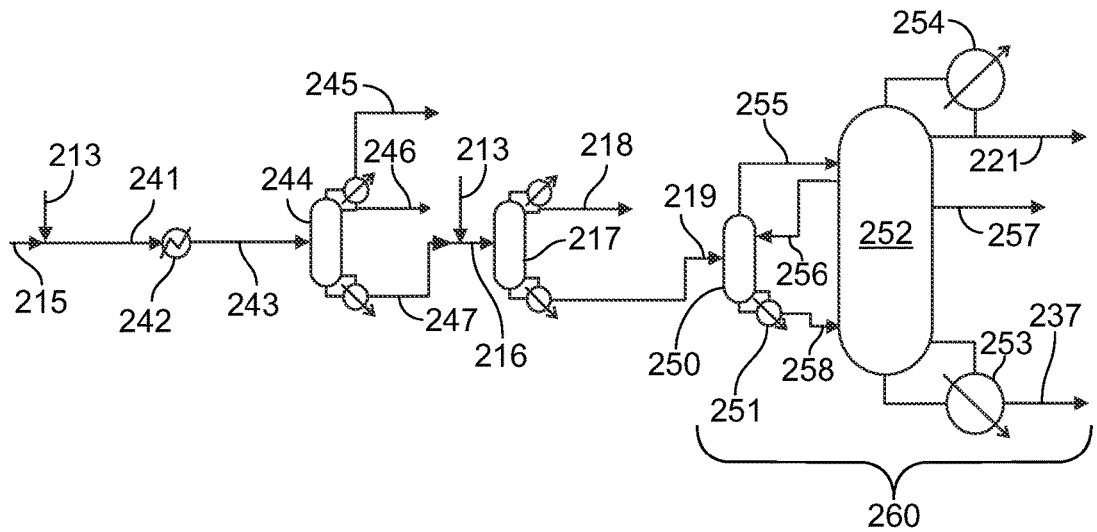
FIG. 2 shows a separation scheme for separating streams concentrated in light ends, benzene, toluene, C8 aromatics, and C9+ aromatics. The scheme includes a reboiled prefractionation column fed by the bottoms stream of a benzene column that includes toluene, C8 aromatics, and C9+ aromatics. The top and bottom streams of the reboiled prefractionation column are fed to the sidedraw column, which produces a sidedraw column top stream including toluene, a sidedraw column side stream including C8 aromatics, and a sidedraw column bottom stream including C9+ aromatics.

Turning now to FIG. 2, a TOL/A9+ TA unit reactor (not shown) effluent stream (Stream 215) may be combined with an extraction unit (not shown) extract stream (Stream 213) to produce a stabilizer column feed stream (Stream 241). The stream 241 may be preheated in a heat exchanger 242 to produce a preheated stream (Stream 243) that is directed to a stabilizer column 244. The heat used to preheat Stream 241 may be derived from a warm process stream available within the aromatics complex. The stabilizer column 244 produces a vapor overhead stream (Stream 245) that includes light vapor hydrocarbons, a bottoms stream (Stream 247) that includes benzene, TOL, C8A, and C9A+, and may produce a liquid overhead stream (Stream 246), which may be a benzene drag stream including benzene and non-aromatic benzene co-boilers.

Stream 247 may be combined with an extraction unit (not shown) extract stream (Stream 213) including benzene and toluene to produce a benzene column feed stream (Stream 216). Stream 216 is directed to benzene column 217 that produces an overhead stream (Stream 218) including benzene and a bottoms stream (Stream 219) including TOL, C8A, and C9A+.

Stream 219 is directed to a distillation apparatus 260 having a prefractionation column 250, including a reboiler 251, and a sidedraw column 252. The prefractionation column 250 produces an overhead stream (Stream 255) that is directed as a feed to the sidedraw column 252. In one embodiment, the overhead stream 255 is preferably a vapor stream, but may be a liquid stream if the prefractionation column 250 has an overhead condenser, or it may be both a vapor and liquid stream. The prefractionation column 250 also produces a liquid bottoms stream (Stream 258) that is directed as feed to sidedraw column 252.

The sidedraw column 252 produces several streams, including a liquid stream (Stream 256) used as reflux to the prefractionation column 250, an overhead stream (Stream 221) including TOL and substantially free of C8A+, a sidedraw stream (Stream 257) including A8, and substantially free of TOL and A9+, and a bottoms stream (Stream 237) including C9A+ and substantially free of A8−. The stream including TOL (Stream 221) may be recycled to a TOL/A9+ TA unit (not shown). A bottoms stream including A9+(Stream 237) may be directed to an A9 column (not shown) which may produce an overhead stream including A9 and some A10 that may be recycled to a TOL/A9+ TA unit, and a bottoms stream including C10+ that is substantially free of A9 that may be used as, for example, a fuel. Sidedraw column 252 includes a reboiler 253 and one or more condensers 254. The condensers may be used to reboil other columns such as stabilizer column 244, benzene column 217, and/or used to generate steam.

Figure 3:
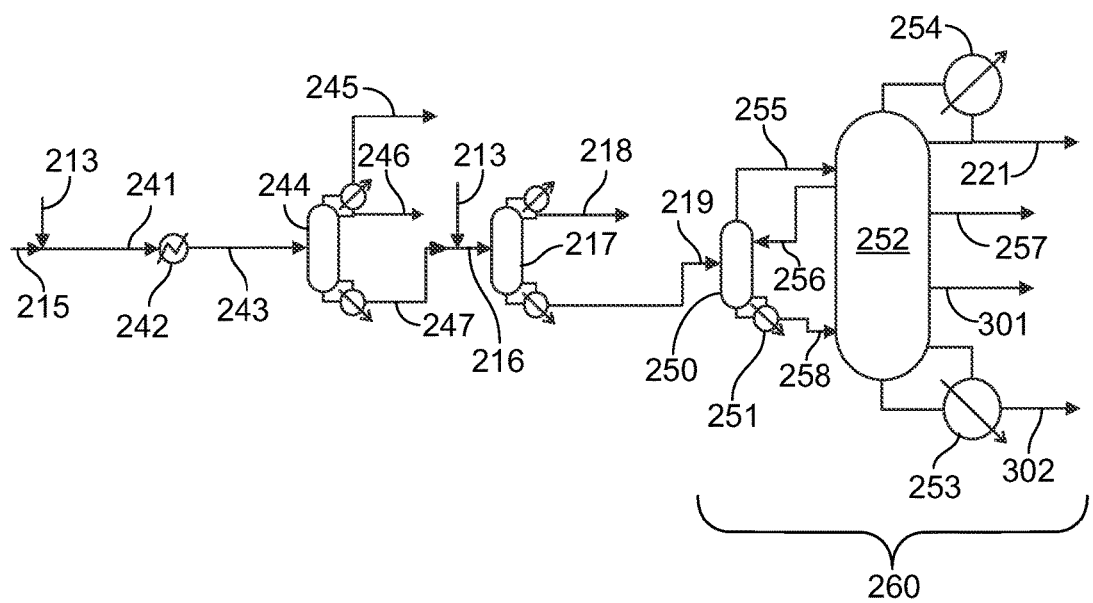
FIG. 3 shows a scheme wherein the A9+ material for recycle to the TOL/A9+TA reactor is taken as an additional sidedraw of the sidedraw column. The bottoms stream of the sidedraw column includes C10+.

FIG. 3 is identical to FIG. 2, except (1) an additional sidedraw stream (Stream 301) is taken from the sidedraw column 252 including mainly A9 and some A10 for recycle to the TOL/A9+ TA reactor, and 2) the sidedraw column bottoms stream (Stream 302) including C10+ that may be used as, for example, a fuel. This embodiment eliminates the need for a separate A9 column and further reduces energy and capital for an aromatics complex. The stream including A8 and substantially free of TOL and A9+(Stream 257) may be directed to a pX recovery section for recovery of pX product.

Various embodiments of the prefractionation column and the sidedraw column including examples of tray locations for feed streams 255 and 258 to the sidedraw column, and withdrawal of the reflux stream 256 and the sidedraw stream 257 are provided in the Examples In some embodiments, the prefractionation column and the sidedraw column may be combined into a single shell dividing wall column with a reboiler for the prefractionation side.

As shown in the examples, the combination of the prefractionation (PREFRAC) column and the sidedraw column (SD-COL) can be designed to meet specifications for TOL and A9+ in the A8 sidedraw stream, such that this stream can be sent directly to a unit that separates pX either by selective adsorption or by crystallization.

In some aspects of the methods and apparatuses disclosed here, the sidedraw column, and consequently the prefractionation column are designed to operate at overhead pressures sufficiently high that condensing overhead vapors of the sidedraw column can be used to reboil the benzene column, the stabilizer column, and/or generate steam in order to save additional energy. One skilled in the art will recognize that the temperature of the condensing overhead vapors of a column with a total condenser, such as the SD-COL is related to the overhead pressure of that column. Similarly the bottoms temperature of a column is related to the pressure of that column, and thus column pressure determines the minimum temperature of the heating medium that can be used to reboil that column. The pressure of saturated steam is related to the temperature of the heating medium required to generate that steam. In all cases, the higher the pressure, the higher the temperature. The temperature of the condensing overhead vapors of a first column must be higher than the temperature at the bottom of a second column which is being reboiled by the first column, and it must be higher by an amount that provides a sufficient driving force for heat transfer. Thus, the overhead pressure of the sidedraw column (SD-COL), and consequently of the prefractionation (PREFRAC) column may be increased to provide a temperature of the condensing overhead vapors of the SD-COL that is greater than about 5 to about 25 degrees Celsius, more preferably greater than about 10 to about 15 degrees Celsius higher than the temperature of the bottoms of a column that these vapors are being used to reboil, or the saturation temperature of the steam that is being generated. Increasing column pressure beyond that which provides such temperature differences is possible, but will increase the wall thickness required for the column, and thus, its cost.

If the condensing vapors of the SD-COL are being used to reboil the benzene column, then, the overhead pressure of the SD-COL may be increased, for example, above about 50 psia (345 kPa absolute). If steam is of value for heating process streams within the aromatics complex or for export to other units, it is preferable to increase the pressure of the prefractionation and sidedraw columns such that steam can be generated from the condensing overhead vapors of the sidedraw column. Generating steam recovers some of the energy put into the column reboilers as useful energy. To generate medium pressure (10 barg) steam, the overhead pressure of the SD-COL may be increased above about 115 psia (793 kPa absolute). If the condensing overhead vapors of the SD-COL are only being used to generate low pressure (25 psia) steam, then the SD-COL overhead pressure would only need to be increased to above about 22 psia (152 kPa absolute). If the condensing overhead vapors of the sidedraw column are only used to reboil the stabilizer column, then the overhead pressure of the SD-COL can be increased to above about 115 psia (793 kPa absolute).

In some embodiments of the methods and apparatuses disclosed herein, the effluent from a TOL/A9+ reactor is separated by the fractionation schemes of FIG. 2 or 3 described above, which are designed to produce an A8 sidedraw stream that meets the specification of less than 500 ppmw A9+ suitable for feeding directly into a unit that separates pX by selective adsorption. In various embodiments, the A8 sidedraw stream contains less than about 2 wt % TOL and more particularly less than about 1.5 wt % TOL, some of which may be recovered via a TOL finishing column within the selective adsorption unit (not shown).

In some embodiments shown in FIGS. 2 and 3, the stabilizer column 244 is designed as a dehexanizer column where non-aromatic benzene co-boilers are removed in the overhead streams 245 and 246. In this case, Stream 218 may meet specifications for salable benzene product. In other embodiments, the stabilizer column 244 may be designed as a depentanizer where C5– hydrocarbons are removed in overhead streams 245 and 246, and the stream concentrated in benzene (Stream 218) or the stabilizer bottoms stream 247 is directed to an extraction unit for removal of non-aromatic benzene co-boilers.

Units that separate pX by crystallization can tolerate much higher levels of A9+ in their feed. Commercial pX crystallization units operate with as much as 2 wt % A9+ or even higher. In another embodiment of this disclosure, the effluent from a TOL/A9+ reactor is separated by the fractionation schemes of FIGS. 2 and 3 described above designed to produce an A8 sidedraw stream that contains less than about 2 wt/o A9+, in particular less than about 1.5 wt % A9+, and more particularly less than about 1.0 wt % A9+ that is suitable for feeding directly into a pX separation section that separates pX by crystallization. Embodiments employing a crystallization unit for pX separation will require less energy for separation than embodiments employing a selective adsorption unit for pX recovery.

In other embodiments, aromatics complexes including various combinations of conventional toluene disproportionation (TDP) units, selective toluene disproportionation (STDP) units that produce xylene isomers rich in pX, and/or TOL/A9+ benefit from the separation scheme of this disclosure.

EXAMPLES

The Examples that follow are set forth for explanatory purposes only, and are not to be taken as limiting the disclosure.

A pX unit C7– (light aromatics) stream including benzene and TOL and a TOL/A9+ condensed reactor effluent stream having the component mass fractions shown in Table 1 are used in the examples. The condensed TOL/A9+ reactor effluent stream contains 640 ppmw naphthalene. The compositions are typical, but as is known to those skilled in the art, the compositions and the flow rates depend on many variables including reformate composition, and the relative size of the pX unit and the TOL/A9+ unit.

TABLE 1

Typical compositions of reactor effluent and pX unit stream

| | TOL/A9+ Reactor Effluent | pX Unit Light Aromatics |
|---|---|---|
| C5 Paraffins | 0.0011 | 0.0245 |
| Other Lights and Paraffins | 0.0308 | 0.0612 |
| Bz | 0.0865 | 0.7095 |
| TOL | 0.3792 | 0.1947 |
| EB | 0.0095 | 0.0013 |
| pX | 0.0755 | 0.0031 |
| mX | 0.1660 | 0.0052 |
| oX | 0.0767 | 0.0004 |
| MEB | 0.0139 | 0.0000 |
| TMB | 0.1340 | 0.0000 |
| DEB | 0.0004 | 0.0000 |
| DMEB | 0.0028 | 0.0000 |
| Other A10+ | 0.0235 | 0.0000 |
| Flow Rate, lb/hr | 705512 | 45556 |

In all examples, this mixture is preheated and sent to a stabilizer column that removes light ends, and then to a benzene column where a stream concentrated in benzene is taken overhead for sale as high purity benzene or as feed to an extraction unit, where the benzene is further purified by removal of a primarily non-aromatic raffinate stream. The performances of all columns, including the compositions and conditions of all column product streams are simulated using an ASPEN Plus® process simulator of Aspen Technology, Inc. For all examples, the design of the stabilizer column and benzene column remains the same. Thus, the feed rate and composition of the benzene column bottoms remains the same. Typical specifications for the benzene column are 98% benzene recovery in the overhead, and 400 ppmw of TOL with base component Bz. The feed rate, composition, and temperature of the benzene column bottoms stream are provided in Table 2.

The calculated absorbed duty of the benzene column for all examples obtained from ASPEN Plus® simulations is 79.5 MMBTU/hr (23.3 MW), and the calculated benzene column bottoms temperature is about 150° C. The calculated absorbed duty of the stabilizer column is 37.7 MMBTU/hr (11.0 MW), and the calculated stabilizer bottoms temperature is about 184° C.

TABLE 2

Benzene column bottoms stream feed rate, composition, and temperature

| | |
|---|---|
| Others | 0.0019 |
| Bz | 0.0027 |
| TOL | 0.4271 |
| EB | 0.0108 |
| pX | 0.0851 |
| mX | 0.1870 |
| oX | 0.0866 |
| MEB | 0.0158 |
| TMB | 0.1531 |
| DEB | 0.0005 |
| DMEB | 0.0032 |
| A10+ | 0.0262 |
| Feed Rate, lb/hr | 615,507 |
| Temperature, F. | 301.7 |

Example 1: Separation Scheme for Producing an A8 Stream Suitable for Sending Directly to a Unit for Recovery of pX by Selective Adsorption Example 1 demonstrates production of mixed xylenes via further fractionation of the benzene column bottoms stream following the fractionation scheme of FIG. 1.

The benzene column bottoms stream is fed to a toluene column simulated to have 52 theoretical stages with the feed to stage 26. The pressure of the vapor leaving the top tray is set to 62.3 psia (430 kPa absolute) and the condenser is assumed to have a pressure drop of 5 psi (34.5 kPa). Design specifications are placed on the column simulation of 0.5 wt % C8A in the TOL overhead stream and 1 wt % TOL amongst the C8A in the column bottoms stream. The calculated absorbed reboiler duty from the simulation is 152.6 MMBTU/hr (44.7 MW). The temperature of the condensed overhead vapors of the column is 166.2° C., and the calculated duty of the condenser is 125.1 MMBTU/hr (36.7 MW), which are sufficient to reboil the benzene column.

The toluene column bottoms stream is passed to a xylene splitter (XS) column simulated to have 122 theoretical stages with feed to theoretical stage 91 from the top. The pressure of the vapor leaving the top tray is set at 85 psia (586 kPa) such that the condensing overhead vapors have a temperature sufficient to reboil the extract and raffinate columns of a unit that separates pX by selective adsorption. Design specifications are placed on the xylene splitter column simulation of 0.05 wt % (500 ppmw) A9+ in the C8A overhead stream and 1 wt/o C8A in the C9A+ column bottoms stream. The calculated absorbed column reboiler duty from the simulation is 112.8 MMBTU/hr (33.1 MW).

Thus, a combined absorbed reboiler duty of 265.4 MMBTU/hr (77.8 MW) for the TOL column and the XS column is required to perform the desired separation of the benzene column bottoms stream into a TOL stream, a C8A stream and an A9+ stream where the C8A stream contains 1 wt % TOL and meets a specification of 500 ppm A9+ such that this stream can be sent directly to a selective adsorption unit for separation of pX.

The A9+ stream may be directed to an A9 column which may produce an overhead stream including A9 and some A10 that may be recycled to a TOL/A9+ TA unit, and a bottoms stream including C10+ that is substantially free of A9 that may be used as, for example, a fuel.

Example 2: Separation Scheme for Producing an A8 Stream Suitable for Sending Directly to a Unit for Recovery of pX by Crystallization Example 2 demonstrates production of mixed xylenes via further fractionation of the benzene column bottoms stream following the fractionation scheme of FIG. 1.

The design of the benzene and toluene columns is the same as for Example 1. The benzene column bottoms stream is fed to a toluene column simulated to have 52 theoretical stages with the feed to stage 26. The pressure of the vapor leaving the top tray is set to 62.3 psia (430 kPa absolute) and the condenser is assumed to have a pressure drop of 5 psi (34.5 kPa). Design specifications are placed on the column simulation of 0.5 wt/o C8A in the TOL overhead stream and 1 wt % TOL amongst the C8A in the column bottoms stream. The calculated absorbed reboiler duty from the simulation was 152.6 MMBTU/hr (44.7 MW). The temperature of the condensed overhead vapors of the column is 166.2° C. and the calculated duty of the condenser was 125.1 MMBTU/hr (36.7 MW), which are sufficient to reboil the benzene column.

The toluene column bottoms stream is passed to a xylene splitter (XS) column simulated to have 122 theoretical stages with feed to theoretical stage 91 from the top. As in Example 1, a design specification is placed on the xylene splitter column simulation of 1 wt % C8A in the C9A+ column bottoms stream. However, because a crystallization unit can tolerate a higher concentration of A9+ in the feed to crystallization, the specification for A9+ in the A8 stream is relaxed to 1 wt % A9+. This lowers the calculated required absorbed column reboiler duty slightly to 107.0 MMBTU/hr (31.4 MW).

Thus, for this example, a combined absorbed reboiler duty of 259.6 MMBTU/hr (76.1 MW) for the TOL column and the XS column is required to perform the desired separation of the benzene column bottoms stream into a TOL stream, a C8A stream and an A9+ stream where the C8A stream contains 1 wt % TOL and 1 wt % A9+ such that this stream can be sent directly to a crystallization unit for separation of pX.

The A9+ stream may be directed to an A9 column which may produce an overhead stream including A9 and some A10 that may be recycled to a TOL/A9+ TA unit, and a bottoms stream including C10+ that is substantially free of A9 that may be used, for example, as fuel.

Example 3: Separation Scheme for Producing an A8 Stream Suitable for Sending Directly to a Unit for Recovery of pX by Selective Adsorption The separation scheme for this Example is shown in FIG. 2, and was simulated via ASPEN. The design of the stabilizer and benzene columns is the same as for Examples 1 and 2. Various combinations of design parameters for the prefractionation column and sidedraw column are implemented. Combinations of design variables with corresponding column performance parameters are summarized in Table 3 for some cases where energy savings can be achieved relative to Example 1 while meeting specifications of less than 1.5 wt/o TOL and less than 500 ppmw of A9+ in the A8 stream, such that the A8 stream can be sent to a selective adsorption unit for separation of pX without the need for further fractionation. The combined absorbed duty of the prefractionation (PREFRAC) and sidedraw (SD-COL) columns of Example 3 represents the duty required to separate the Bz column bottoms into a TOL stream suitable for recycle to the TOL/A9+ reactor, an A9+ stream, and an A8 stream that can be sent directly to a selective adsorption unit for pX recovery without the need for further fractionation. The A9+ stream may be directed to an A9 column which may produce an overhead stream including A9 and some A10 that may be recycled to a TOL/A9+ TA unit, and a bottoms stream including C10+ that is substantially free of A9 that may be used as, for example, a fuel.

Tables 3 and 4 show examples of design variables. "SD-COL, No. of stages" is the number of theoretical stages for this column in the simulation, including one stage for the reboiler and one stage for the condenser. "SD-COL, Stg-RFLX1" is the sidedraw column stage where a liquid sidedraw is taken for reflux to the prefractionation column. "SD-COL, Stg-OVHDV1" is the stage in the sidedraw column to which the overhead vapor from the prefractionation column is directed. "SD-COL. Stg-BTTMLIQ1" is the sidedraw column stage to which the bottoms liquid from the prefractionation column is directed. "SD-COL. Stg-C8A" is the sidedraw column stage from which the C8A is taken as a sidedraw.

TABLE 3

Design variables for Example 3

| | Case | | | |
|---|---|---|---|---|
| | 3.1 33d-23 | 3.2 33d-29 | 3.3 33d-35 | 3.4 33d-36 |
| REFLX1 Stream flow rate, lbmol/hr | 3300 | 3300 | 3300 | 3300 |
| SD-COL | | | | |
| No. of Stages | 112 | 112 | 112 | 112 |
| Stg-RFLX1 | 34 | 34 | 34 | 34 |
| Stg-OVHDV1 | 34 | 34 | 34 | 34 |
| Stg-BTTMLIQ1 | 86 | 86 | 86 | 86 |
| Stg-C8A | 56 | 56 | 56 | 56 |
| PREFRAC-COL | | | | |
| No. of Stages | 40 | 40 | 40 | 40 |
| Feed Tray | 20 | 20 | 20 | 20 |
| Wt fract TOL in A8 | 0.01123 | 0.01057 | 0.00997 | 0.00250 |
| Wt fract A9+ in A8 | 0.00047 | 0.00037 | 0.00032 | 0.00046 |
| Reboiler Duties, MMBTU/hr | | | | |
| SD-COL | 120 | 130 | 140 | 140 |
| PREFRAC | 118 | 118 | 118 | 120 |
| Total | 238 | 248 | 258 | 260 |
| Fraction of Duty of TOL and XS Col Duties of Example 1 | 0.897 | 0.934 | 0.972 | 0.980 |

As shown by the data in Table 3, the fractionation scheme of this disclosure can reduce energy required to do the separation by over 10%.

Example 4: Separation Scheme for Producing an A8 Stream Suitable for Sending Directly to a Unit for Recovery of pX by Crystallization The separation scheme for this example is shown in FIG. 2 and was simulated via ASPEN. The designs of the stabilizer and benzene columns are the same as for Examples 1 and 2. The overhead pressure of the SD-COL is assumed to be 62.3 psia (430 kPa absolute) with an assumed 5 psi (34.5 kPa) pressure drop through the condenser. Various combinations of design parameters for the prefractionation column (PREFRAC) and sidedraw column (SD-COL) are tried. Combinations of design variables with corresponding column performance parameters are summarized in Table 4 for some cases where energy savings can be achieved relative to Example 2, while meeting specifications of less than 1.0 wt % TOL and less than 1 wt % of A9+ in the A8 stream, such that the A8 stream can be sent to a crystallization section for separation of pX without the need for further fractionation. The A9+ stream may be directed to an A9 column which may produce an overhead stream including A9 and some A10 that may be recycled to a TOL/A9+ TA unit, and a bottoms stream including C10+ that is substantially free of A9 that may be used as, for example, a fuel.

Example 5: Separation Scheme for Producing an A8 Stream Suitable for Sending Directly to a Unit for Recovery of pX by Crystallization with SD-COL Pressure Increased to Produce Medium Pressure Steam The separation scheme for this Example is shown in FIG. 2 and was simulated via ASPEN. For this case, the pressure of the PREFRAC and SD-COL columns are increased to allow production of medium pressure (10 barg) steam from the condensing overhead vapors of the SD-COL. The overhead pressure of the SD-COL is assumed to be 116.8 psia (805 kPa absolute) with an assumed 5 psi (34.5 kPa) pressure drop through the condenser. This gives a SD-COL overhead temperature entering the condenser of 203° C., and a condenser outlet temperature of about 201° C., which is sufficient to generate 10 barg steam, which has a saturation temperature of about 185° C. These condenser temperatures

TABLE 4

Design variables for Example 4.

| | Case | | | | | | | | |
|---|---|---|---|---|---|---|---|---|---|
| | 4.1 (5-9) | 4.2 (5-14) | 4.3 (5-15) | 4.4 (5-16) | 4.5 (7-9) | 4.6 (7-10) | 4.7 (8-6) | 4.8 (8-10) | 4.9 (9-5) |
| REFLX1 Stream low rate, lbmol/hr | 2700 | 2700 | 2700 | 2700 | 2700 | 2700 | 3000 | 3000 | 3000 |
| SD-COL | | | | | | | | | |
| No. of Stages | 90 | 90 | 90 | 90 | 90 | 90 | 90 | 90 | 90 |
| Stg-RFLX1 | 26 | 26 | 26 | 26 | 26 | 26 | 26 | 26 | 26 |
| Stg-OVHDV1 | 26 | 26 | 26 | 26 | 26 | 26 | 26 | 26 | 26 |
| Stg-BTTMLIQ1 | 66 | 66 | 66 | 66 | 66 | 66 | 66 | 66 | 66 |
| Stg-C8A | 40 | 40 | 40 | 40 | 40 | 40 | 40 | 40 | 36 |
| PREFRAC-COL | | | | | | | | | |
| No. of Stages | 40 | 40 | 40 | 40 | 40 | 40 | 40 | 40 | 40 |
| Feed Tray | 15 | 15 | 15 | 15 | 20 | 20 | 20 | 20 | 20 |
| Wt fract TOL in A8 | 0.00135 | 0.00886 | 0.00122 | 0.00114 | 0.00268 | 0.00177 | 0.00183 | 0.00638 | 0.00626 |
| Wt fract A9+ in A8 | 0.00911 | 0.00695 | 0.00723 | 0.00911 | 0.00763 | 0.00889 | 0.00750 | 0.00842 | 0.00806 |
| Reboiler Duties, MMBTU/hr | | | | | | | | | |
| SD-COL | 85 | 90 | 90 | 90 | 85 | 85 | 80 | 85 | 80 |
| PREFRAC | 114 | 112 | 114 | 116 | 114 | 116 | 120 | 116 | 118 |
| Total | 199 | 202 | 204 | 206 | 199 | 201 | 200 | 201 | 198 |
| Fraction of Duty of TOL and XS Col Duties of Example 2 | 0.755 | 0.766 | 0.774 | 0.781 | 0.755 | 0.763 | 0.759 | 0.763 | 0.751 |

As shown by the data in Table 4, the fractionation scheme of this disclosure can save close to 25% of the energy required by Example 2.

Note that the energy requirement to meet specifications of the A8 sidedraw stream necessary to feed a pX crystallization section for the cases of Example 4 are lower than the energy requirement to meet specifications of the A8 sidedraw stream necessary to feed the A8 stream to a pX selective adsorption section. Also note that fewer stages are required for Example 4 than for Example 3. Reboiler duty is related to vapor and liquid traffic in the tower. The lower duty required for Example 4 relative to Example 3 means smaller diameter columns are needed. Lower duty also means less $CO_2$ greenhouse gas emission.

are also sufficient to reboil the benzene column which has a bottoms temperature of about 150° C., and sufficient to reboil the stabilizer column, which has a bottoms temperature of 185° C.

The design of the stabilizer and benzene columns is the same as for Examples 1 and 2. Various combinations of design parameters for the PREFRAC and SD-COL are implemented. Combinations of design variables with corresponding column performance parameters are summarized in Table 5 for some cases where energy savings can be achieved relative to Example 2, while meeting specifications of less than 1.5 wt % TOL and less than 1.5 wt % of A9+ in the A8 stream, such that the A8 stream can be sent to a crystallization unit for separation of pX without the need for further fractionation. The A9+ stream may be directed to an A9 column which may produce an overhead stream including A9 and some A10 that may be recycled to a TOL/A9+ TA unit, and a bottoms stream including C10+ that is substantially free of A9 that may be used as, for example, a fuel.

In this Example 6, a stream including mainly A9 and some A10 is taken as an additional sidedraw stream (Stream 301 of FIG. 3) for recycle to the TOL/A9+ TA reactor, and the bottoms stream of the sidedraw column (Stream 302 of FIG. 3) including C10+ and substantially free of A9 and may be

TABLE 5

Design variables for Example 5

| | Case | | | | | | | |
|---|---|---|---|---|---|---|---|---|
| | 5.1 (27-60) | 5.2 (27-93) | 5.3 (30-39) | 5.4 (30-50) | 5.5 (33-31) | 5.6 (33-63) | 5.7 (36-32) | 5.8 (36-43) |
| REFLX1 Stream flow rate, lbmol/hr | 2700 | 2700 | 3000 | 3000 | 3300 | 3300 | 3600 | 3600 |
| SD-COL | | | | | | | | |
| No. of Theoretical Stages | 90 | 90 | 90 | 90 | 90 | 90 | 90 | 90 |
| Stg-RFLX1 | 26 | 26 | 26 | 26 | 26 | 26 | 26 | 26 |
| Stg-OVHDV1 | 26 | 26 | 26 | 26 | 26 | 26 | 26 | 26 |
| Stg-BTTMLIQ1 | 66 | 66 | 66 | 66 | 66 | 66 | 66 | 66 |
| Stg-C8A | 40 | 40 | 40 | 40 | 40 | 40 | 40 | 40 |
| PREFRAC-COL | | | | | | | | |
| No. of Stages | 40 | 40 | 40 | 40 | 40 | 40 | 40 | 40 |
| Feed Tray | 15 | 15 | 15 | 15 | 20 | 20 | 20 | 20 |
| Wt fract TOL in A8 | 0.00534 | 0.00458 | 0.01130 | 0.01084 | 0.00538 | 0.00810 | 0.00651 | 0.00616 |
| Wt fract A9+ in A8 | 0.01409 | 0.01201 | 0.01264 | 0.01091 | 0.01151 | 0.00647 | 0.00975 | 0.00734 |
| Reboiler Duties, MMBTU/hr | | | | | | | | |
| SD-COL | 115 | 130 | 105 | 110 | 100 | 115 | 100 | 105 |
| PREFRAC | 128 | 128 | 130 | 130 | 136 | 134 | 138 | 138 |
| Total | 243 | 258 | 235 | 240 | 236 | 249 | 238 | 243 |
| Fraction of Duty of TOL and XS Col Duties of Example 2 | 0.922 | 0.979 | 0.892 | 0.910 | 0.895 | 0.945 | 0.903 | 0.922 |
| Condenser Duty, MMBTU/hr | 191.73 | 206.73 | 183.75 | 188.74 | 184.72 | 197.72 | 186.72 | 191.72 |
| Steam Credit, MMBTU/hr | 120.27 | 135.27 | 112.29 | 117.28 | 113.26 | 126.26 | 115.26 | 120.26 |
| Fraction of Duty of TOL and XS Col Duties of Example 2 With MP Steam Credit | 0.466 | 0.466 | 0.466 | 0.466 | 0.466 | 0.466 | 0.466 | 0.466 |

As shown by the data in Table 5, for all of these cases, the total duty of the PREFRAC and SD-COL is less than that of the total duty of TOL and XS columns of Example 2 by as much as 10.2%. When credit is given for MP steam export, the net energy required to do the separation is less than half of that of Example 2.

Example 6: Separation Scheme for Producing an A8 Stream Suitable for Sending Directly to a Unit for Recovery of pX by Crystallization with SD-COL Pressure Increased to Produce Medium Pressure Steam and with an Additional Sidedraw Column C9A+ Stream The separation scheme for this Example is shown in FIG. 3 and was simulated via ASPEN. Conditions and design considerations for the stabilizer, benzene column, prefractionation column, and sidedraw column are the same as for Example 5 Case 5.3 (as shown in Table 5) with the following exceptions.

In Example 5, the sidedraw column had 90 theoretical stages, and a stream including A9+ was taken as a bottoms stream. The A9+ stream of Example 5 may be directed to an A9 column which may produce an overhead stream including A9 and some A10 that may be recycled to a TOL/A9+ TA unit, and a bottoms stream including C10+ that is substantially free of A9 that may be used as for example a fuel.

used as for example, a fuel. In this example, the stream including mainly A9 and some A10 is referred to as the C9A+ stream. The additional sidedraw (Stream 301) is taken as liquid from theoretical stage 90 from the top. Additional stages are added below this sidedraw which increases the total number of theoretical stages to the number shown in Table 6. Other relevant stages of the sidedraw column remain the same as per Example 5 Case 5.3. The reboiler duty of the prefractionation column and the sidedraw column were fixed as per Example 5 Case 5.3 at 130 MMBTU/hr (38.1 MW) and 105 MMBTU/hr (30.8 MW) respectively. Thus, in Example 6, separation of the C9A+ stream takes place with no additional duty relative to Example 5 Case 5.3.

To avoid the need for a separate A9 column, it is desirable for the C9A+ stream to contain essentially all of the MEB and TMB in the combined C9A+ and C10+ streams, and a high fraction of the DEB, DMEB, and TTMB. However, it is desirable to separate a high fraction of the naphthalene in the combined C9A+ and C10+ streams into the C10+ stream since naphthalene and heavy components of the C10+ stream can foul exchangers within the TOL/A9+ TA unit and lead to a high deactivation rate of the TA unit catalyst.

Simulation results for several cases are provided in Table 6.

TABLE 6

Simulation Results for Example 6.

| Case Number | 6-110-83 | 6-110-70 | 6-110-80 | 6-100-70 | 6-100-80 |
|---|---|---|---|---|---|
| No. Stages in SD-COL | 110 | 110 | 110 | 100 | 100 |
| Stg. For C9A+ withdrawal | 90 | 90 | 90 | 90 | 90 |
| % Recov. In C9A | | | | | |
| MEB | 100.0 | 100.0 | 100.0 | 99.5 | 99.7 |
| TMB | 99.9 | 100.0 | 100.0 | 99.0 | 99.4 |
| DEB | 97.5 | 98.5 | 99.2 | 92.9 | 95.9 |
| DMEB | 86.3 | 91.4 | 95.2 | 84.2 | 90.4 |
| TTMB | 60.0 | 70.0 | 80.0 | 70.0 | 80.0 |
| Naphthalene | 20.8 | 21.8 | 23.2 | 29.7 | 36.5 |
| Total Mass | 93.6 | 94.9 | 96.1 | 94.1 | 95.8 |

As shown in this example, recovery of desirable components MEB and TMB in the CA9+ stream for recycle to the TOL/A9+ reactor can be near 100%. Recovery of the desirable components DEB, DMEB, and TTMB may also be very high. Recovery of naphthalene in the C9A+ stream is fairly low and thus, a high fraction of the naphthalene is recovered in the C10+ stream. Recovery of desirable components MEB, TMB, DEB. DMEB, and TTMB in the C9A+ stream increases with the specified recovery of TTMB in the C9A+ sidedraw stream. However, naphthalene recovery in this stream also increases. Naphthalene recovery also increases with a reduction in the number of stages added below the C9A+ sidedraw stream. One skilled in the art will appreciate that the optimal number of stages and TTMB recovery will depend on local feedstock and byproduct prices, energy cost, and local cost of capital.

While the invention has been described above according to various embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A process comprising the steps of:
   (a) providing a prefractionation column feed stream comprising toluene, C8 aromatics, and C9+ aromatics to a reboiled prefractionation column to produce a prefractionation column top stream and a prefractionation column bottom stream; and
   (b) providing the prefractionation column top stream and the prefractionation column bottom stream to a sidedraw column to produce a sidedraw column top stream comprising toluene, a sidedraw column first side stream comprising C8 aromatics, a sidedraw column second side stream comprising a liquid, and a sidedraw column bottoms stream comprising C9+ aromatics; and feeding the sidedraw second side stream to the prefractionation column as reflux.

2. The process of claim 1, further comprising recovering paraxylene from the sidedraw column first side stream comprising C8 aromatics to produce a paraxylene product stream and a paraxylene lean stream.

3. The process of claim 1, further comprising recycling at least a portion of the sidedraw column top stream to a transalkylation reactor.

4. The process of claim 1, further comprising recycling at least a portion of the sidedraw column bottoms stream comprising C9+ aromatics to a transalkylation reactor.

5. The process of claim 1, wherein the sidedraw column top stream is substantially free of C8 aromatics.

6. The process of claim 1, wherein the sidedraw column side stream comprising C8 aromatics is substantially free of toluene and C9+ aromatics.

7. The process of claim 1, wherein the sidedraw column receives the prefractionation column top stream as a vapor stream without condensation.

* * * * *